(12) United States Patent
Yamanaka et al.

(10) Patent No.: US 6,508,760 B2
(45) Date of Patent: Jan. 21, 2003

(54) ENDOSCOPE FOR OPTICALLY VARIABLE POWER USING MOVING TIME AS POSITION INFORMATION

(75) Inventors: Kazuhiro Yamanaka, Omiya (JP); Mitsuru Higuchi, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 149 days.

(21) Appl. No.: 09/797,945

(22) Filed: Mar. 5, 2001

(65) Prior Publication Data
US 2001/0021798 A1 Sep. 13, 2001

(30) Foreign Application Priority Data
Mar. 13, 2000 (JP) ........................................ 2000-068383

(51) Int. Cl.[7] .................................................. A61B 1/06
(52) U.S. Cl. ...................... 600/168; 600/167; 600/118; 348/240.99; 348/65
(58) Field of Search ................................. 600/168, 160, 600/109, 167, 173, 118; 348/240.99, 240.1, 240.2, 240.3, 65, 75; 359/697, 698

(56) References Cited

U.S. PATENT DOCUMENTS

| | | | | |
|---|---|---|---|---|
| 5,420,632 A | * | 5/1995 | Yamagiwa | 348/240.3 |
| 6,046,770 A | * | 4/2000 | Uemura et al. | 348/240.99 |
| 6,117,071 A | * | 9/2000 | Ito et al. | 600/168 |
| 6,387,046 B2 | * | 5/2002 | Yamanaka et al. | 600/168 |
| 6,413,207 B1 | * | 7/2002 | Minami | 600/109 |
| 6,422,995 B2 | * | 7/2002 | Akiba | 600/167 |
| 6,425,858 B1 | * | 7/2002 | Minami | 600/168 |
| 6,447,447 B1 | * | 9/2002 | Mitsumori | 600/167 |
| 6,450,949 B1 | * | 9/2002 | Farkas et al. | 600/168 |

* cited by examiner

Primary Examiner—Teresa Walberg
Assistant Examiner—Fadi H. Dahbout
(74) Attorney, Agent, or Firm—Snider & Associates; Ronald R. Snider

(57) ABSTRACT

A movable lens is provided at the tip of an electroscope, and an optically enlarged image can be observed by moving the movable lens by a motor. A microcomputer measures the entire moving time from a far end to a near end of the movable lens, and the moving time is used as the variable power position information about the movable lens. The variable power position information is displayed by a meter display, etc. on a monitor. Thus, an encoder, etc. is not required.

5 Claims, 5 Drawing Sheets

ENDOSCOPE FOR OPTICALLY VARIABLE POWER USING MOVING TIME AS POSITION INFORMATION

BACKGROUND OF THE INVENTION

This application claims the priority of Japanese Patent Application No. 2000-68383 filed on Mar. 13, 2000 which is incorporated herein by reference.

1. Field of the Invention

The present invention relates to an endoscope, and more specifically to a device capable of observing an object by optically enlarging the image of the object.

2. Description of the Prior Art

Recently, an endoscope (electronic endoscope), etc. has been provided with a movable lens for variable power in an objective system of a scope tip, the movable lens is driven by an actuator, etc. so that an image of the object can be optically enlarged. The optically enlarged image is captured by a solid-state image pickup device such as a CCD (charge coupled device), etc., and an enlarged image of the object is displayed on the monitor by performing various image processes by a processor device on a video signal (image signal) output from the CCD. In the above mentioned optically variable power mechanism, a target portion can be observed by enlarging the image of the portion for the magnification of 70 through 100.

BRIEF SUMMARY OF THE INVENTION

Object of the Invention

In the optically variable power function of the above mentioned endoscope, an encoder, etc. is mounted to detect the moving position of a movable lens for variable power. That is, a correct value of magnification can be obtained by the encoder detecting the position in the optical axis direction of the movable lens moving by a drive mechanism.

However, the above mentioned movable lens is built in the optical objective system of the thin tip of the endoscope. If the encoder for detecting the position is also built in the tip, the diameter of the thin tip is necessarily larger.

The present invention has been developed to solve the above mentioned problems, and aims at providing an endoscope capable of detecting the moving position of a movable lens for variable power without an encoder, etc.

Summary of the Invention

To attain the above mentioned purpose, the present invention includes a movable lens, provided at the tip of an endoscope, for observing an optically magnified image, a drive circuit for driving the movable lens, and a control circuit, which uses the moving time of the movable lens from a predetermined end as the variable power position information of the movable lens by measuring an entire moving time of the variable power movable lens moving between driving ends, for performing various controlling processes according to the variable power position information about the movable lens.

It is desired that the control circuit initializes the moving range of the movable lens when the first variable power switch is operated after electric power is applied.

The control circuit can also display the variable power position information specified by the moving time on the monitor.

With the above mentioned configuration, the entire moving time of the movable lens, for example, from the near end to the far end, for variable power is measured before a variable power operation. When a near switch is pressed, the decrement count value of the moving time from the far end is the position information about the movable lens. When a far switch is pressed, the increment count value is the position information. The entire moving time count is allotted to a predetermined stage to display the variable power position information, and the magnification (status) of an image is stepwise displayed on the monitor. Furthermore, the variable power position information is also used as the information as a notification that the movable lens is reaching the network and the far end. With the prediction of the approach to the ends, the reduction of a drive brake and a drive speed can be prevented.

DETAILED DESCRIPTION OF THE PREFERRED EMBODIMENTS

Figure 1:
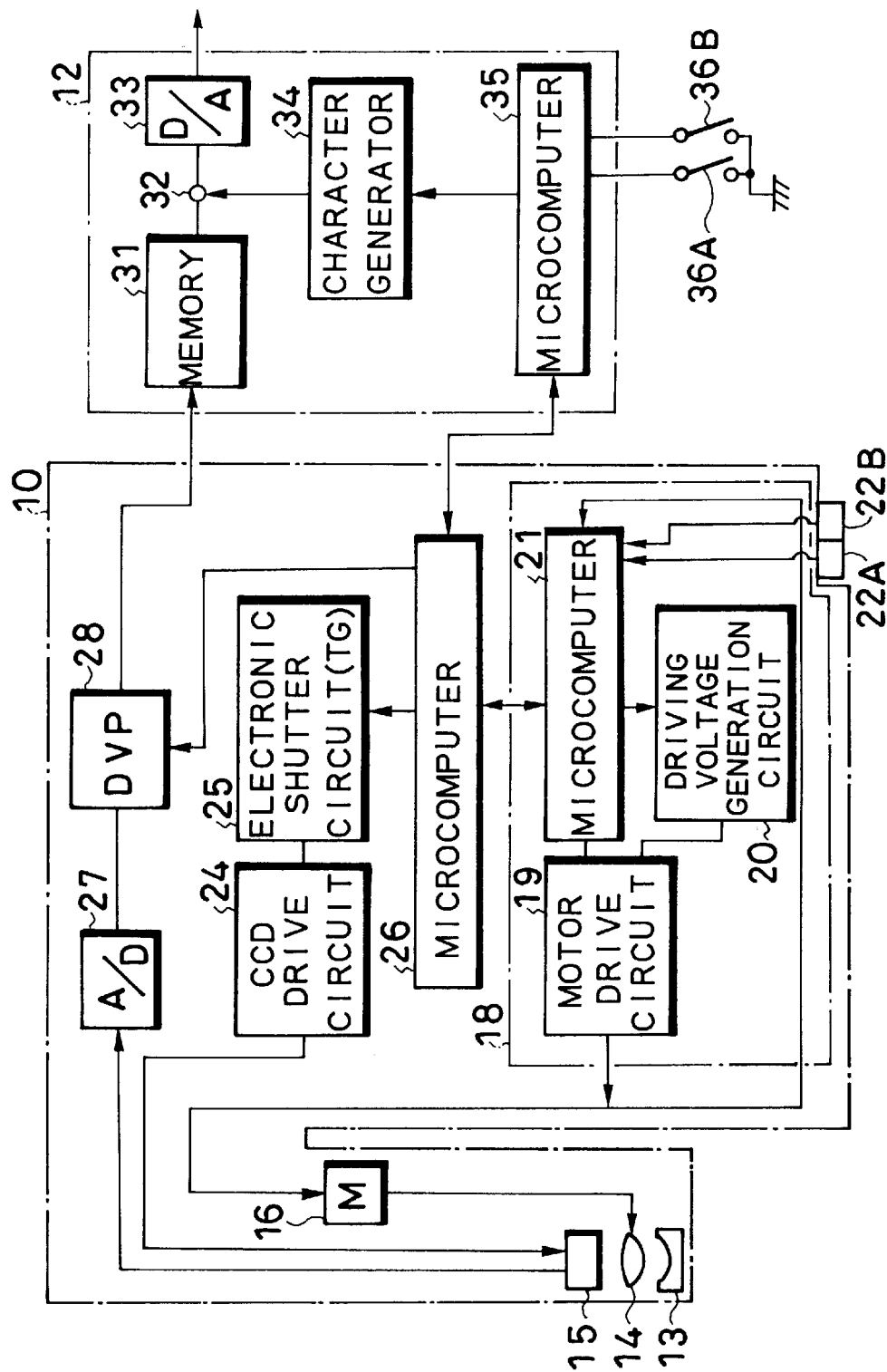
FIG. 1 is a block diagram of the configuration of the electronic endoscope according to an embodiment of the present invention.

FIG. 1 shows the configuration of the electronic endoscope according to an embodiment of the present invention. This apparatus comprises an electroscope (electronic endoscope) 10 is mounted on a processor device 12 as freely attachable/detachable through a connector. In FIG. 1, the tip of the electroscope 10 contains an objective system with variable power comprising a fixed lens (or lens group) 13 and a movable lens (or lens group) 14. A CCD 15 is arranged as an image pickup device for receiving a light from the objective system.

For example, a motor 16 is connected to the above mentioned movable lens 14 through a drive unit, the rotating drive power of the motor 16 is transmitted to the tip through a linear transmission unit, and the rotating movement is converted into a linear movement to move the movable lens 14. Additionally, the motor 16 can be mounted on the tip to rotate a cylindrical cam (axis), thereby moving the movable lens 14. The above mentioned motor 16 can be replaced with another actuator for directly drive the movable lens 14.

Furthermore, a variable power drive circuit 18 for driving the motor 16 (or actuator) is provided in the electroscope 10. The variable power drive circuit 18 comprises a motor drive circuit 19, a driving voltage generation circuit 20, and a microcomputer 21. In addition, the operating unit, etc. of the electroscope 10 contains a near (N) switch 22A for an enlarging operation and a far (F) switch 22B for a reducing operation as a variable power switch. These operation signals are provided for the microcomputer 21. That is, if the N switch 22A or the F switch 22B is operated, the motor drive circuit 19 transmits the rotation driving voltage to the motor 16 based on the control of the microcomputer 21 and the driving voltage from the driving voltage generation circuit 20. As a result, the motor 16 rotates in a predetermined direction. When the movable lens is reaching an end, control is performed to work the brake or reduce the rotation speed of the motor 16.

Figure 2:
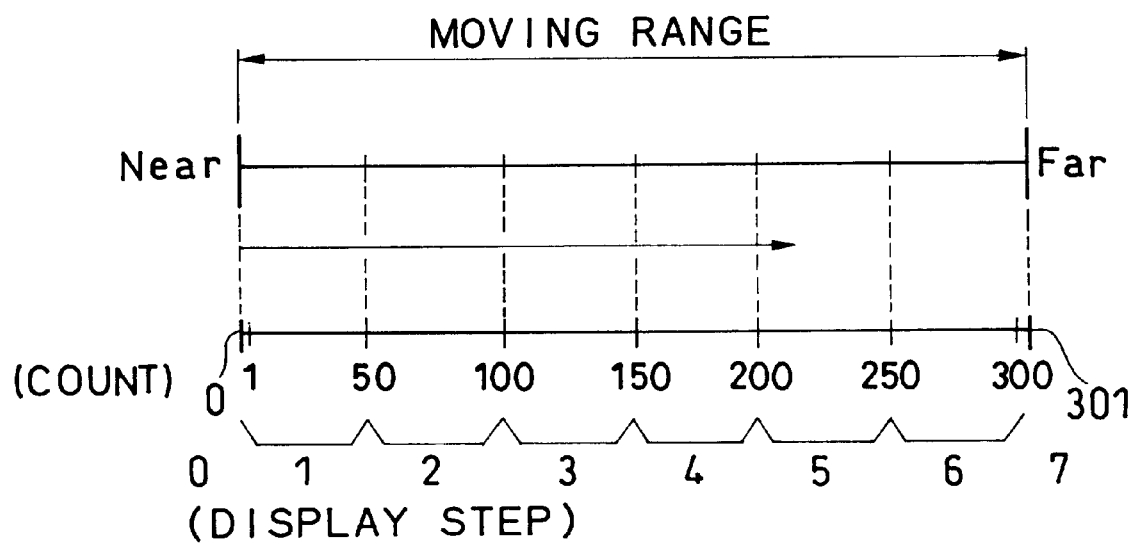
FIG. 2 shows the relationship between the moving range of the movable lens and the time count according to the embodiment of the present invention.

Then, the above mentioned microcomputer 21 measures the entire moving time of the movable lens 14 between the driving ends, and determines the moving position of the movable lens 14 by the moving time count value from the near end (or far end). That is, as shown in FIG. 2, assuming that a time of 301 count (1 count refers to predetermined seconds (10 ms, etc.)) is required to move the movable lens 14 in the entire range from the near end to the far end, the variable power position, that is, the magnification, can be obtained by the count value of 0 to 301 count.

Furthermore, to display a meter, 0 is set as a near point, 301 is set as a far point, and 6 stages of variable power setting areas are set. That is, the variable power setting areas 1, 2, 3, 4, 5, and 6 are respectively set to 1 to 50, 51 to 100, 101 to 150, 151 to 200, 201 to 250, and 251 to 300. For example, when an operation is performed for a 60 count by the N switch 22A from the far end, the movable lens 14 is located at the area 5, that is, the second stage of the variable power position from the far end because the current movable lens 14 is positioned at the count of 241.

In the electroscope 10, a CCD drive circuit 24 for driving the CCD 15, an electronic shutter circuit 25 containing a timing generator (TG), and a microcomputer 26 are provided. Based on the integral control of the microcomputer 26, the electronic shutter circuit 25 controls the signal accumulation time (electronic shutter speed) of the CCD 15, and the image signal accumulated in the CCD 15 in a pixel unit is read by the CCD drive circuit 24. Furthermore, an A/D converter 27 and a digital video processor (DVP) 28 for performing various image processes are provided. The image signal read from the CCD 15 is converted into a digital signal, and then the DVP 28 performs various image processes for amplification, white balance, gamma amendment, etc. by the DVP 28.

On the other hand, the processor device 12 contains image memory 31, a mixer 32, a D/A converter 33, etc. It further comprises a character generator 34 for outputting a character image (characters, graphics) representing the variable power position information displayed on the meter (FIG. 3), and a microcomputer 35. The character image output from the character generator 34 is mixed with the image of an object by the mixer 32.

Figure 3:
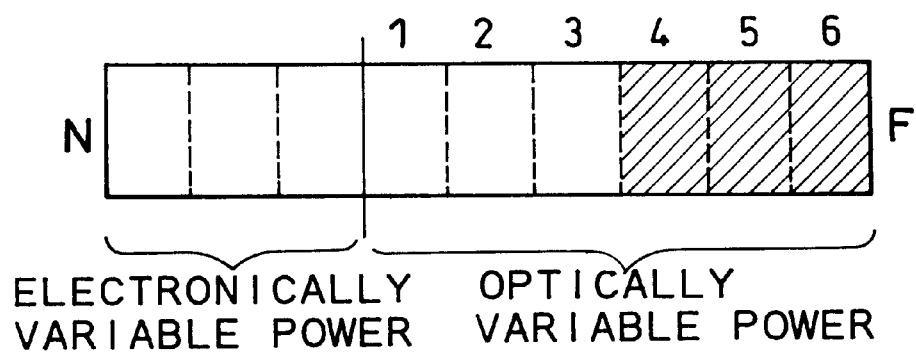
FIG. 3 shows the display of a meter on the monitor indicating the variable power (magnification) of the electronic endoscope according to the embodiment of the present invention.

That is, the processor device 12 also comprises an electronic enlargement (variable power) circuit (not shown) and displays the electronic variable power and the enlargement (magnification) of the optically variable power. For example, as shown in FIG. 3, using a meter display image for sequentially lighting the divided areas in the bar-shaped unit extending in the horizontal direction, the divided areas are sequentially lighted from the far end to the near end with the N (near) positioned at the leftmost end, and the F (far) positioned at the rightmost end. Furthermore, the processor device 12 can also be provided with a foot switch (variable power switch) comprising an N (near) switch 36A and an F (far) switch 36B. These operation control signals are provided for the microcomputer 35.

Figure 4:
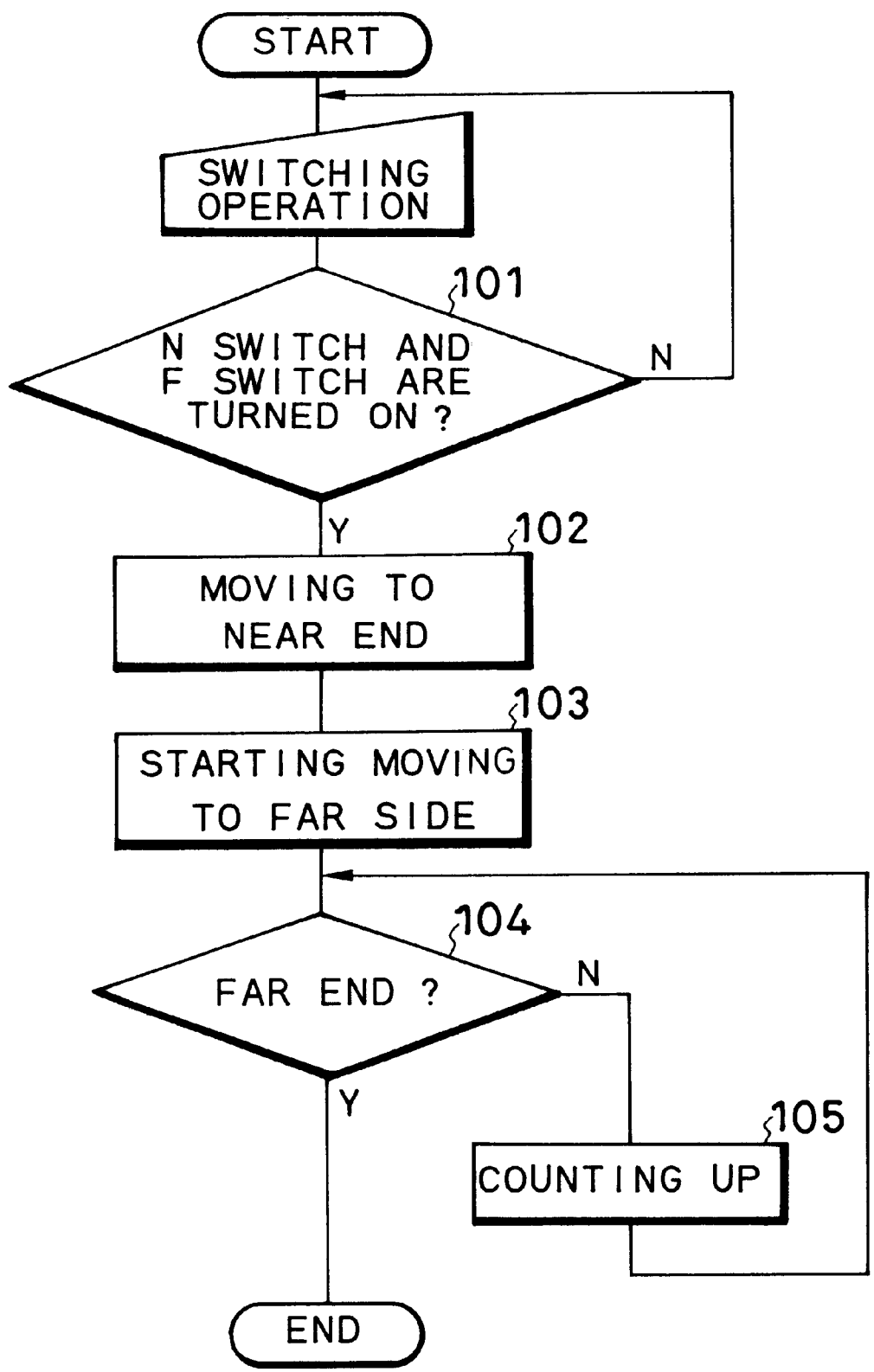
FIG. 4 is a flowchart of the initializing operation for the variable power according to the embodiment of the present invention.

The embodiment is configured as described above, and the effect is described below by referring to FIGS. 4 to 6. When power is applied to the apparatus, and the operation of each switch becomes effective, for example, the N switch 22A (or 36A) or the F switch 22B (or 36B) is pressed in step 101, the movable lens 14 is temporarily moved to the near (N) end in step 102. That is, by the control of the microcomputers 21, 26, and 35, the motor driving voltage is transmitted from the motor drive circuit 19 to the motor 16, thereby moving the movable lens 14 to the N end which is to be confirmed.

Then, in step 103, the movable lens 14 starts moving from the N end to the far (F) end. In step 104, it is determined and detected whether or not the current position of the movable lens 14 is the F end. If no, then the time count is increased by 1 in step 105. If yes, then the operation terminates. Therefore, in step 105, the count value continues increasing until the movable lens 14 moves to the F end. As a result, the time count value from the N end to the F end, for example, 301, is measured. Thus, in this example, the moving range of the movable lens 14 is initialized when a variable power switch 36 is turned ON.

Figure 5:
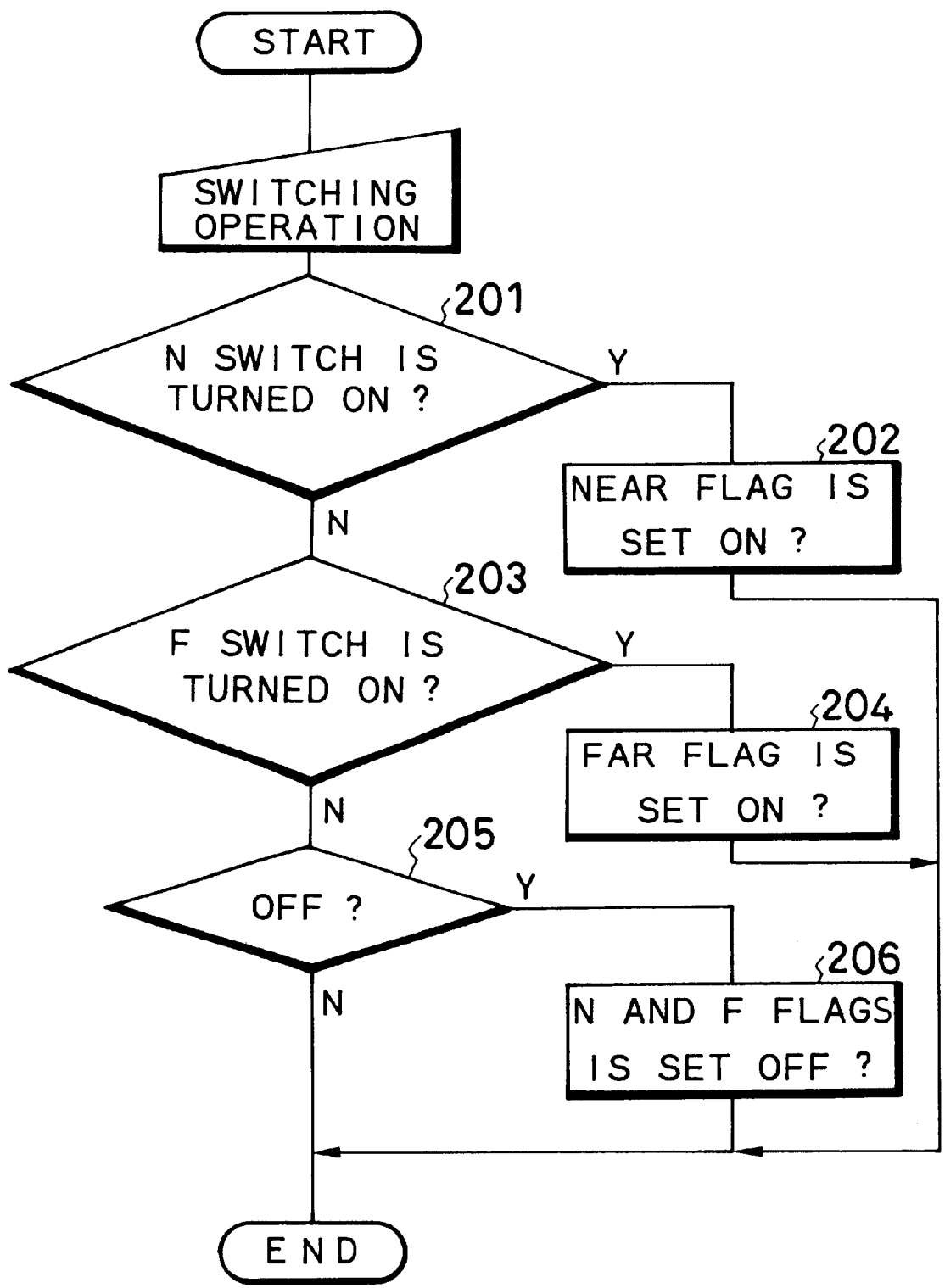
FIG. 5 is a flowchart of the operation for the variable power switch according to the embodiment of the present invention.
Figure 6:
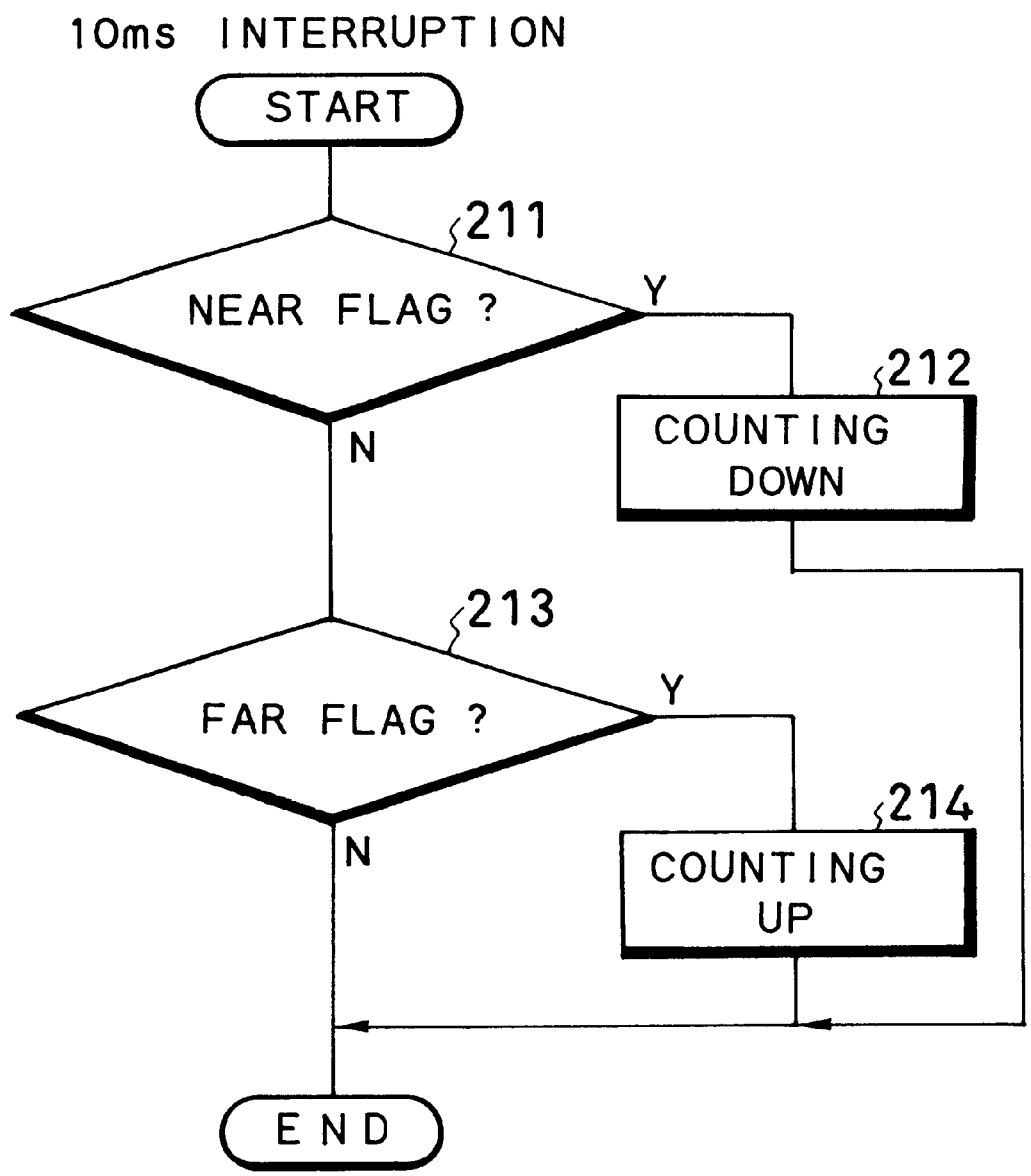
FIG. 6 is a flowchart of the operation for the variable power switch according to the embodiment of the present invention.

Next, as shown in FIG. 5, the microcomputer 21 (26, 35) detects the operation of a variable power switch 22 (36). In step 201, it is determined whether or not the N switch 22A has been pressed. If yes, a near flag is set ON in step 202. In step 203, it is determined whether or not the F switch 22B has been pressed. If yes, a far flag is set on in step 204. In step 205, it is determined whether or not each of the N switches 22A and 22B has been pressed. If yes, the near flag or the far flag is set OFF in step 206. In the interruption routine (every 10 ms) shown in FIG. 6, it is determined in step 211 whether or not the near flag is set (ON). If yes, the time count is decremented by 1 (step 212). In step 213, it is determined whether or not the far flag is set ON. If yes, the time count is incremented by 1 (step 214).

That is, when the N switch 22A is pressed, the value is counted down from 301 at the far end as shown in FIG. 2. When 120 is subtracted, the count value is 181, and a variable power position can be specified by the time count value of 181. By referring to the display level, 181 corresponds to the variable power position at the stage 4 as shown in FIG. 3. According to the variable power meter display formed by the character generator 34, the three positions from the far end are lighted as a chain line. On the other hand, when the F switch 22B is pressed, the values are counted up from the starting value to obtain the time count value as a variable power position. The position of the N end of the variable power can be obtained when the count value reaches 0, and the subsequent enlargement of an image is electronically performed. According to the display of the meter shown in FIG. 3, the electronic magnification is stepwise displayed depending on the electronic variable power.

The above mentioned count value indicates that the movable lens 14 is approaching to the N end of the F end, and the microcomputer 21 instructs the motor drive circuit 19 to use a brake or lower the driving speed, thereby reducing the impact of the driving mechanism when the movable lens 14 reaches the N end or the F end, and realizing smooth driving.

As described above, the image of an object obtained by the optical objective system containing the movable lens 14 is captured by the CCD 15, and the image signal of the CCD 15 is read by the CCD drive circuit 24, and input to the DVP 28 through the A/D converter 27. The DVP 28 performs various image processes, and the results are temporarily stored in the image memory 31 of the processor device 12. The image signal output from the image memory 31 contains the meter display of the variable power formed by the character generator 34 and mixed by the mixer 32. The resultant image signal is provided for the monitor through the D/A converter 33. Therefore, the monitor displays the image in the object with the display of the variable power meter shown in FIG. 3 attached to one of the four corners.

In this example, as shown in FIG. 1, since the variable power drive circuit 18 is provided in the electroscope 10 for variable power, it is not necessary to separately attach the variable power drive circuit 18. Although the electroscope 10 is connected to an old type of processor device, the variable power function can be used.

As described above, according to the present invention, the moving time of the movable lens for variable power from a predetermined end can be used as the variable power position information about the movable lens, and various controlling processes are performed according to the variable power position information. Therefore, the moving position of the movable lens for variable power can be obtained without an encoder, etc., thereby maintaining a smaller diameter of the endoscope. Furthermore, since the variable power position information specified by the moving time is displayed on the monitor, the magnification of the displayed image can be easily determined.

What is claimed is:

1. An endoscope apparatus with an optically variable power function, comprising:

a movable lens, provided at a tip of an endoscope, for observing an optically magnified image;

a drive circuit for driving the movable lens; and a control circuit for measuring an entire moving time of the variable power movable lens moving between driving ends, and using a moving time of said movable lens from a predetermined end as variable power position information of said movable lens to perform various controlling processes based on the variable power position information about said movable lens.

2. The apparatus with an optically variable power function according to claim 1, wherein said control circuit initializes a moving range of said movable lens when a variable power switch is first operated after electric power is applied.

3. The apparatus with an optically variable power function according to claim 1, wherein said control circuit controls displaying variable power position information specified by the moving time of said movable lens on a monitor.

4. The apparatus with an optically variable power function according to claim 3, wherein as the variable power position information, a magnification is displayed by indication changing stepwise.

5. The apparatus with an optically variable power function according to claim 1, wherein said control circuit controls a movement of said movable lens to decelerate the movable lens when said movable lens approaches to an enlargement end or a reduction end according to the variable power position information.

* * * * *